(12) United States Patent
Nakaguma et al.

(10) Patent No.: US 11,427,803 B2
(45) Date of Patent: *Aug. 30, 2022

(54) CELL CULTURE SUBSTRATE

(71) Applicant: DIC Corporation, Tokyo (JP)

(72) Inventors: Hirohide Nakaguma, Sakura (JP); Ayako Isshiki, Sakura (JP)

(73) Assignee: Fujifilm Corporation, Tokyo (JP)

( * ) Notice: Subject to any disclaimer, the term of this patent is extended or adjusted under 35 U.S.C. 154(b) by 412 days.

This patent is subject to a terminal disclaimer.

(21) Appl. No.: 16/467,526

(22) PCT Filed: Dec. 12, 2017

(86) PCT No.: PCT/JP2017/044506
§ 371 (c)(1),
(2) Date: Jun. 7, 2019

(87) PCT Pub. No.: WO2018/116902
PCT Pub. Date: Jun. 28, 2018

(65) Prior Publication Data
US 2019/0367870 A1    Dec. 5, 2019

(30) Foreign Application Priority Data
Dec. 22, 2016  (JP) .............................. JP2016-248890

(51) Int. Cl.
*C12N 5/00* (2006.01)
*C08F 293/00* (2006.01)
*C12M 1/12* (2006.01)

(52) U.S. Cl.
CPC ........ *C12N 5/0068* (2013.01); *C08F 293/005* (2013.01); *C12M 25/14* (2013.01); *C12N 2533/30* (2013.01)

(58) Field of Classification Search
None
See application file for complete search history.

(56) References Cited

U.S. PATENT DOCUMENTS

| | | | | |
|---|---|---|---|---|
| 2014/0212973 A1* | 7/2014 | Nakayama | ........... | C12N 5/0068 435/396 |
| 2016/0101190 A1 | 4/2016 | Russell et al. | | |
| 2017/0029763 A1 | 2/2017 | Takada | | |

FOREIGN PATENT DOCUMENTS

| | | |
|---|---|---|
| CN | 101092471 A | 12/2007 |
| CN | 101205302 A | 6/2008 |
| CN | 101293943 A | 10/2008 |
| CN | 101307123 A | 11/2008 |
| CN | 102056983 A | 5/2011 |
| CN | 103080295 A | 5/2013 |
| CN | 103781812 A | 5/2014 |
| CN | 106317297 A | 1/2017 |
| CN | 108929412 A | 12/2018 |
| CN | 110121552 A | 8/2019 |
| EP | 2292691 A1 | 3/2011 |
| EP | 2330182 A1 | 6/2011 |
| JP | H02-211865 A | 8/1990 |
| JP | 2013-195399 A | 9/2013 |
| JP | 2014-140384 A | 8/2014 |
| WO | 2012/029882 A1 | 3/2012 |
| WO | 2015/093393 A1 | 6/2015 |
| WO | 2016/106033 A1 | 6/2016 |
| WO | 2016/199552 A1 | 12/2016 |

OTHER PUBLICATIONS

A. Mellati et al., "Influence of Polymer Molecular Weight on the in Vitro Cytotoxicity of Poly (N-isopropylacrylamide)," Materials Science and Engineering C, vol. 59, 2016, pp. 509-513. (cited in the ISR).
International Search Report dated Mar. 13, 2018, issued for PCT/JP2017/044506.
Office Action dated Aug. 23, 2018, issued in the corresponding Japanese patent application No. 2018-535908 with its English Machine Translation.
Extended European Search Report dated Aug. 4, 2020, issued in the corresponding European patent application No. 17884382.7.
Office Action dated Mar. 1, 2022, issued in the corresponding Chinese patent application No. 201780079493 4 with its English Machine Translation.
Florian Kafer et al., "LCST and UCST in One: Double Thermoresponsive Behavior of Block Copolymers of Poly (ethylene glycol) and Poly(acrylamide-co-acrylonitrile)," Langmuir 2015, 31, pp. 8940-8946. (cited in the Aug. 4, 2020 Office Action issued for EP17884382.7).
Susumu Saeki et al., "Upper and lower critical solution temperatures in poly (ethylene glycol) solutions," Polymer, vol. 17, Aug. 1976, pp. 685-689. (cited in the Aug. 4, 2020 Office Action issued for EP17884382.7).
Notification of Reason for Refusal dated Jun. 3, 2022, issued for Korean Patent Application No. 10-2019-7014078 and English translation thereof.

* cited by examiner

*Primary Examiner* — Christopher M Rodd
(74) *Attorney, Agent, or Firm* — Locke Lord LLP

(57) ABSTRACT

The present invention is to provide a cell culture substrate including a block polymer including a segment having a lower critical solution temperature and a hydrophobic segment, in which the segment having a lower critical solution temperature has a degree of polymerization of 400 to 10,000. Also provided is a cell culture substrate, in which the hydrophobic segment is obtainable by polymerizing a monomer having a particular structure. Also provided is a cell culture substrate being laminated on a supporting medium. Furthermore, a cell culture substrate having an average film thickness of 1,000 nm or less is provided.

10 Claims, No Drawings

CELL CULTURE SUBSTRATE

TECHNICAL FIELD

The present invention relates to a substrate for use in cell culture.

BACKGROUND ART

In recent years, technologies for culturing animal cells have seen a remarkable progress, and animal cells themselves or products thereof and the like are widely used for research uses and medical uses. When it is intended to culture animal cells in vitro, it is necessary to attach the animal cells to a certain substrate that serves as scaffolding, and in that case, the cells and the substrate are adhered to each other by an adhesive protein coming from the cells or a preliminarily coated scaffolding agent. Therefore, in a case in which these cells are detached from the substrate, it is necessary to destroy the protein between the cells and the substrate using, for example, an enzymatic treatment or the like, and damage to cells and the like have been a problem.

Under such circumstances, there has been suggested a cell culture substrate having a temperature-responsive polymer immobilized on the surface of the substrate. Such a substrate is adhesive to protein at the cell culture temperature; however, when the temperature is lowered, the surface state of the cell culture substrate is changed, and adhesiveness to protein is decreased. Therefore, it is possible to detach cells without an enzymatic treatment (for example, PTL 1).

Furthermore, in PTL 2, it has been suggested that a temperature responsive polymer can be immobilized on the surface of a substrate without requiring large-scale apparatuses such as irradiation with an electron beam, by using a substrate coated on the substrate surface with a block copolymer adopting a structure in which a water-insoluble polymer segment and a temperature-responsive polymer segment are bonded.

However, the block copolymer disclosed in PTL 2 has insufficient water resistance, and there exist a problem that elution occurs from the substrate surface, and a problem that the cell detachability is insufficient.

CITATION LIST

Patent Literature

PTL 1: JP-A-2-211865
PTL 2: WO 2012/029882

SUMMARY OF INVENTION

Technical Problem

It is an object of the present invention to provide a cell culture substrate, with which animal cells can be cultured with high efficiency and the cells obtained after culturing can be detached and harvested in a living condition.

Solution to Problem

The inventors conducted a thorough investigation, and as a result, the inventors found that the above-described problems can be solved by providing a cell culture substrate including a block polymer including a segment having a lower critical solution temperature and a hydrophobic segment, in which the segment having a lower critical solution temperature has a degree of polymerization of 400 to 10,000.

Furthermore, there is provided a cell culture substrate in which the hydrophobic segment is obtainable by polymerizing a monomer represented by the following Formula (1).

[Chem. 1]

In Formula (1), $R^1$ represents a hydrogen atom or a methyl group; and $R^2$ represents any one of a phenyl group, a carboxyalkyl group having an alkyl with 1 to 8 carbon atoms, a carboxyaralkyl group having an aralkyl with 7 to 8 carbon atoms, a group represented by the following Formula (2), or a group represented by the following Formula (3).

[Chem. 2]

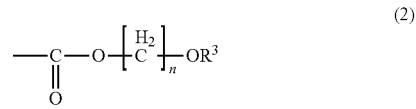

In Formula (2), n represents 2 or 3; and $R^3$ represents an alkyl group having 1 to 3 carbon atoms.

[Chem. 3]

In Formula (3), $R^4$ and $R^5$ each independently represent a hydrogen atom or an alkyl group having 1 to 6 carbon atoms; and the total number of carbon atoms of $R^4$ and $R^5$ is 5 or more.

Advantageous Effects of Invention

The cell culture substrate of the present invention enables culturing of animal cells with high efficiency and enables detachment and harvest of cells after culturing, in a living condition.

DESCRIPTION OF EMBODIMENTS

The present invention is to provide a cell culture substrate including a block polymer including a segment having a lower critical solution temperature and a hydrophobic segment, in which the segment having a lower critical solution temperature has a degree of polymerization of 400 to 10,000.

[Segment Having Lower Critical Solution Temperature]

The segment having a lower critical solution temperature according to the present invention is a segment for the block copolymer, and the segment refers to a segment composed of a polymer that dissolves in water when the temperatures reaches a certain temperature or lower.

The segment having a lower critical solution temperature according to the present invention is a polymer that dissolves in water when the temperature reaches a certain temperature or below as described below. Examples of the polymer having a lower critical solution temperature include the following 1) and 2).

1) A homopolymer having a lower critical solution temperature by polymerizing.

2) A copolymer of a hydrophobized monomer and a hydrophilic monomer.

The polymer 1) is a homopolymer segment by polymerizing only a monomer that gives a homopolymer having a lower critical solution temperature. Examples of the monomer that gives a homopolymer having a lower critical solution temperature include N-isopropyl (meth)acrylamide, N-n-propyl (meth) acrylamide, N-cyclopropyl (meth) acrylamide, N-ethoxyethyl (meth) acrylamide, N-tetrahydrofurfuryl (meth) acrylamide, N-ethylacrylamide, N-ethyl-N-methylacrylamide, N,N-diethylacrylamide, N-methyl-N-n-propylacrylamide, N-methyl-N-isopropylacrylamide, N-acryloylpiperidine, and N-acryloylpyrrolidine. These monomers may be utilized singly, or a plurality of kinds thereof may be utilized simultaneously.

The segment obtainable by polymerizing a monomer that gives a homopolymer having a lower critical solution temperature according to 1) can conveniently produce a polymer having a lower critical solution temperature. However, these monomers have low adhesiveness to plastic surfaces and have a problem that when brought into contact with water, a coated polymer layer is easily detachable. However, since the cell culture substrate of the present invention contains a hydrophobic segment, the cell culture substrate has excellent water resistance, and therefore, the culture substrate can be used without detachment.

The copolymer 2) is a copolymer of a hydrophobized monomer and a hydrophilic monomer. In order for a copolymer of a hydrophobized monomer and a hydrophilic monomer to have a lower critical solution temperature, examples include:

2-1) a case in which the hydrophilic monomer is a monomer that gives a homopolymer having a lower critical solution temperature; and 2-2) a copolymer (B1) of monomer (a) represented by the following Formula (1) and a hydrophilic amide-based vinyl monomer (b), a copolymer (B2) of the above-described or monomer (a) and monomer (c) represented by the following Formula (2), or a copolymer (B3) of monomer (a) and a polyethylene glycol chain-containing monomer (d) represented by the following Formula (3).

[Chem. 4]

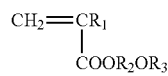

(1)

wherein $R_1$ represents a hydrogen atom or a methyl group; $R_2$ represents an alkylene group having 2 or 3 carbon atoms; and $R_3$ represents an alkyl group having 1 or 2 carbon atoms.

[Chem. 5]

(2)

wherein $R_4$ represents a hydrogen atom or a methyl group; and $R_5$ represents an alkylene group having 2 or 3 carbon atoms.

[Chem. 6]

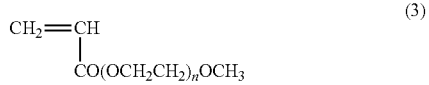

(3)

wherein n represents an integer of 2 to 20.

Examples of the hydrophilic amide-based monomer (b) include dimethylacrylamide, acrylamide, methylacrylamide, and ethylacrylamide.

A hydrophobized monomer is a monomer that is water-soluble originally but becomes insoluble in an aqueous solvent when polymerized. In a case in which such a monomer is included in a copolymer, a cell culture substrate that has excellent water resistance and is not easily detachable from the supporting medium, can be obtained.

Regarding the hydrophobized monomer, a compound represented by Formula (1), diacetone acrylamide, polypropylene glycol (meth)acrylate, methoxy diethylene glycol acrylate, and methoxy triethylene glycol acrylate may be mentioned. These may be used singly, or a plurality of kinds thereof may be used simultaneously. Among them, 2-methoxyethyl acrylate, 2-ethoxyethyl acrylate, and 3-methoxypropyl acrylate are preferred, and 2-methoxyethyl acrylate and 2-ethoxyethyl acrylate are particularly preferred.

In the case of the copolymer segment disclosed in 2-2), the lower critical solution temperature of the copolymer segment thus obtainable can be widely controlled by the types or ratio of the monomers. Furthermore, by changing the types or ratio of the monomers according to the type of cells, the copolymer segment acquires more satisfactory cell adhesiveness and proliferation properties, and cells can be cultured, which is preferable. For example, as the ratio of monomer (b or c or d) is increased with respect to monomer (a), the lower critical solution temperature of the copolymer thus obtainable is shifted toward the higher temperature side. This ratio and the lower critical solution temperature are in an almost linear relationship. Since the cell culture temperature is usually 37° C., it is preferable to prepare the copolymer such that the lower critical solution temperature of the copolymer thus obtainable is near 20° C. to 32° C.

In regard to the block polymer of the present invention, the degree of polymerization of the segment having a lower critical solution temperature is 400 to 10,000. In a case in which the degree of polymerization is less than 400, cell detachability becomes poor, and in a case in which the degree of polymerization is larger than 10,000, since the cell culture substrate has inferior water resistance, the substrate is easily detached from the supporting medium.

A preferred polymerization is 1,000 to 8,000, and within this range, an excellent balance is achieved between cell detachability and culture efficiency. A value of 3,000 to 6,000 is particularly preferred.

[Hydrophobic Segment]

The block polymer of the present invention has a hydrophobic segment. Meanwhile, according to the present specification, the term "hydrophobicity" for a segment of the block polymer means that a polymer formed from the segment has a solubility at 25° C. in water of less than 0.5 g/100 mL. A hydrophobic segment includes at least a monomer unit of a hydrophobic monomer.

Since the block polymer of the present invention has a hydrophobic segment, even though the block polymer has a segment having a lower critical solution temperature, which causes poor water resistance, the block polymer has excellent water resistance and has excellent adhesiveness to a supporting medium.

The hydrophobic monomer is not particularly limited as long as it is a monomer that is hydrophobized after polymerization; however, preferred examples include monomers represented by the following Formulae (1) to (3). In addition, these hydrophobic monomers may be used singly, or two or more kinds thereof may be used in combination.

[Chem. 7]

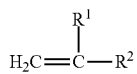

(1)

In Formula (1), $R^1$ represents a hydrogen atom or a methyl group; and $R^2$ represents any one of a phenyl group, a carboxyalkyl group having an alkyl with 1 to 8 carbon atoms, a carboxyaralkyl group having an aralkyl with 7 to 8 carbon atoms, a group represented by the following Formula (2), or a group represented by the following Formula (3).

[Chem. 8]

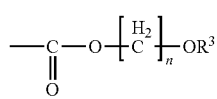

(2)

In Formula (2), n represents 2 or 3; and $R^3$ represents an alkyl group having 1 to 3 carbon atoms.

[Chem. 9]

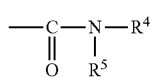

(3)

In Formula (3), $R^4$ and $R^5$ each independently represent a hydrogen atom or an alkyl group having 1 to 6 carbon atoms; and the total number of carbon atoms of $R^4$ and $R^5$ is 5 or more.

Among these, as the monomer represented by Formula (1) is used, a polymer segment thus obtainable becomes hydrophobic, and the cell culture substrate acquires excellent water resistance and adhesiveness to a supporting medium, which is preferable.

Among them, preferred examples include ethyl acrylate, butyl acrylate, and styrene, and a particularly preferred example is butyl acrylate.

[Block Polymer]

The block polymer of the present invention is a polymer including a segment having a lower critical solution temperature and a hydrophobic segment as described above.

When the segment having a lower critical solution temperature is designated as A, and the hydrophobic segment is designated as B, the block polymer of the present invention may be a diblock type of AB or a triblock type of ABA or BAB, or may be a polymer having a larger number of segments. Preferably, the block polymer is a diblock type or triblock type polymer, and particularly preferably a diblock type polymer.

[Method for Producing Block Polymer]

The method for producing the block polymer is not particularly limited, and any known method can be employed. Above all, the method is preferably precise radical polymerization; more preferably reversible addition fragmentation chain transfer (RAFT) polymerization, atom transfer radical polymerization (ATRP), or nitroxide-mediated polymerization (NMP); and even more preferably RAFT polymerization.

[Other Admixtures]

The cell culture substrate of the present invention may include admixtures in addition to the block polymer. For example, the cell culture substrate may include an antiseptic agent, an antibacterial agent, a coloring material, a fragrance, an enzyme, a sugar, a protein, a peptide, an amino acid, a cell, a DNA, a salt, a water-soluble organic solvent, a surfactant, a polymer compound, and a leveling agent.

[Cell Culture Substrate]

The shape of the cell culture substrate of the present invention is not particularly limited as long as cells can be cultured thereon, and cultured cells can be easily detached therefrom by a low temperature treatment. Examples include a film-shaped substrate, a dish-shaped substrate, a bottle-shaped substrate, a tube-shaped substrate, a thread-shaped or rod-shaped substrate having a thickness of 5 nm to 5 mm, a bag-shaped substrate, a multi-well plate-shaped substrate, a microflow channel-shaped substrate, a porous membrane-shaped or network-shaped substrate (for example, TRANSWELL or a cell strainer), and a spherical-shaped substrate having a particle size of preferably 10 to 2,000 μm, and more preferably 100 to 500 μm.

Furthermore, the film thickness of the cell culture substrate of the present invention is, in a state of being sufficiently dried at a temperature equal to or higher than the lower critical temperature, preferably 1,000 nm or less, and more preferably 500 nm or less.

The cell culture substrate of the present invention may be used alone as a simple substance. Preferably, the cell culture substrate is used in the form of a cell culture container material including a supporting medium and the substrate formed on the supporting medium. It is because when used in the form of a cell culture container material, the cell culture substrate has excellent convenience for transportation, storage, and the like, and can be used directly as a culture container or a carrier for culture.

The material of the supporting medium on which the cell culture substrate of the present invention is laminated is not particularly limited as long as the culture substrate can be sufficiently adhered thereto, cell culture can occur on the culture substrate thus adhered, and cultured cells can be easily detached by a low temperature treatment. For example, a styrene-based resin such as polystyrene; a polyolefin-based resin such as polypropylene; a polyurethane-based resin; a polycarbonate; polyethylene terephthalate (PET); a polysulfone-based resin; a fluororesin; a polysaccharide natural polymer such as cellulose; an inorganic material such as glass or ceramic; and a metallic material such as stainless steel or titanium, are suitably used.

The shape of the supporting medium is not particularly limited, and any shape that can serve as a supporting medium of the cell culture substrate of the present invention is acceptable. Examples include a film-shaped supporting medium, a membrane-shaped supporting medium, a plate-shaped supporting medium, a spherical-shaped supporting medium, a polygonal-shaped supporting medium, a rod-shaped supporting medium, a dish-shaped supporting medium, a bottle-shaped supporting medium, a tubular-shaped supporting medium, a needle/thread-shaped supporting medium, a fiber-shaped supporting medium, a bag-shaped supporting medium, a multi-well plate-shaped supporting medium, a microflow channel-shaped supporting medium, a porous membrane-shaped supporting medium, and a network-shaped supporting medium (for example, TRANSWELL or a cell strainer). A shape combining these is acceptable, and an irregularly shaped supporting medium that does not have a particular shape is also acceptable.

Furthermore, the cell culture substrate of the present invention may be integrated with a supporting medium and used as a cell culture container material, or the cell culture substrate may be detached from the supporting medium and used alone.

As a preferable method for forming the cell culture substrate of the present invention, a method of coating a coating agent including the block polymer of the present invention on the above-mentioned supporting medium may be employed.

<Coating Agent>

The coating agent includes a block polymer and a solvent. In addition to those, if necessary, the coating agent may further include additives and the like.

[Block Polymer]

Regarding the block polymer, since the above-mentioned block polymer is used, further explanation will not be repeated here.

Meanwhile, only one kind of block polymer may be included, or two or more kinds of block polymers having different configurations may be included.

The content of the block polymer is preferably 0.01% to 90% by mass, and more preferably 0.1% to 50% by mass, with respect to the total mass of the coating agent. When the content of the block polymer is 0.01% by mass or more, it is preferable from the viewpoint that the coating film thus obtainable is likely to exhibit surface hydrophilicity. On the other hand, when the content of the block polymer is 90% by mass or less, since the viscosity is low, it is preferable from the viewpoint that coating suitability is enhanced.

[Solvent]

The solvent that can be included in the coating agent is not particularly limited, and any known solvent can be used.

A specific example of the solvent may be water or an organic solvent.

Examples of the organic solvent include alcohol-based solvents such as methanol, ethanol, isopropyl alcohol, butanol, sec-butanol, iso-butanol, and tert-butanol; ether-based solvents such as tetrahydrofuran and 1,4-dioxane; ketone-based solvents such as cyclohexanone and methyl isobutyl ketone; nitrile-based solvents such as acetonitrile; amide-based solvents such as dimethylformamide and dimethylacetamide; dimethyl sulfoxide; dioxirane; and pyrrolidone. Among these, as an organic solvent, it is preferable to use an alcohol-based solvent, and it is more preferable to use methanol, ethanol, propanol, isopropyl alcohol, or tert-butanol.

Among the solvents described above, it is preferable that the solvent is water or an alcohol-based solvent, and is more preferably methanol, ethanol, propanol, isopropyl alcohol, or tert-butanol.

The above-mentioned solvents may be used singly, or two or more kinds thereof may be used in combination.

The content of the solvent in the coating agent is preferably 10% to 99.99% by mass, more preferably 50% to 99.9% by mass, and even more preferably 80% to 99.5% by mass, with respect to the total mass of the coating agent. When the content of the solvent is 10% by mass or more, the viscosity of the coating agent solution becomes lower, and therefore, it is preferable from the viewpoint of having excellent coating suitability. On the other hand, when the content of the solvent is 99.99% by mass or less, the thickness of the coating film after coating does not become too thin, and thus it is preferable.

[Additives]

The coating agent may include additives according to the purpose of use.

The additives are not particularly limited, and any known additives can be used. Specific examples include an excipient, a surfactant, a plasticizer, an antifoaming agent, a pigment, an antioxidant, an antibiotic substance, an ultraviolet absorber, a crystal nucleating agent, a crystallization accelerator, a stabilizer, and an antibacterial agent. These additives may be used singly, or two or more kinds thereof may be used as mixtures.

The method of coating the coating agent is not particularly limited, and examples include a spray coating method, a flow coating method, and an immersion method.

Furthermore, in a case in which the substrate is in a tubular shape, a method of passing the coating agent liquid therethrough may be considered. At this time, after the passage of the coating agent liquid, usually, a solvent is passed through so as to remove any excess coating agent inside the tube.

The drying conditions are also not particularly limited, and the coating film may be subjected to natural drying or heated drying. The drying temperature in the case of heated drying may vary depending on the coating agent used; however, the drying temperature is preferably 30° C. to 70° C., and more preferably 40° C. to 60° C. By controlling drying, a coating film having some of the solvent remaining therein can be obtained.

[Animal Cells]

The cell culture substrate of the present invention enables suitable culturing of animal cells. Regarding the animal cells, the origin may be any animal, and examples of the animal include human being, mouse, and monkey. The type of cell is not particularly limited; however, examples include epithelial cells (corneal epithelial cells, and the like), endothelial cells (human umbilical vein endothelial cells, and the like), fibroblastic cells (human skin fibroblasts, mouse fibroblasts, and the like), blood corpuscles, contractile cells (skeletal muscle cells, cardiac muscle cells, and the like), blood and immune cells (red blood corpuscles, macrophages, and the like), nerve cells (neurons, glial cells, and the like), pigment cells (retinal pigment cells, and the like), liver cells, cartilage cells, osteoblastic cells, and stem cells (ES cells, iPS cells, hematopoietic stem cells, skin stem cells, germ stem cells, EC cells, EG cells, and neural stem cells).

In a case in which animal cells are cultured with the present cell culture substrate, culture can be carried out by allowing a culture medium and cells to coexist in the present cell culture substrate and maintaining the system at a temperature appropriate for culture. Regarding the culture medium, any culture medium appropriate for the cell type may be selected. During culture, the culture medium may or may not be exchanged in accordance with the duration of culture, and this may be selected as appropriate. Furthermore, the culture medium may be in a stationary state or in a perfusion state, and any method suitable for the cells to be cultured may be selected.

EXAMPLES

Hereinafter, the present invention will be specifically described by way of Examples; however, the scope of the present invention is not intended to be limited to these Examples.

Synthesis Example 1

Synthesis of Block Polymer 1

0.59 g of butyl acrylate (manufactured by Wako Pure Chemical Industries, Ltd.), 0.0065 g of 2-(dodecylthiocarbonothioylthio)propanoic acid as a RAFT agent, 0.0036 g of dimethyl 2,2'-azobis(2-methylpropionate), 9.0 g of t-butanol, and 1.0 g of water were subjected to sufficient nitrogen bubbling so as to remove oxygen, and then the mixture was stirred for 7 hours at 70° C. Thereby, a first reaction liquid was obtained. The conversion of butyl acrylate in this stage was 81%.

Next, a mixture of 10.53 g of N-isopropylacrylamide (hereinafter, NIPAM; manufactured by KJ Chemicals Corp.), 49.86 g of t-butanol, and 5.54 g of water was subjected to sufficient nitrogen bubbling, and then the mixture was added to the reaction liquid described above. The resultant mixture was further stirred for 20 hours at 70° C. After completion of the reaction, 66.7 g of methanol was added to the reaction liquid, and thereby an AB type temperature-responsive block polymer solution was obtained. The conversions of this block polymer were measured by NMR, and the conversion of butyl acrylate was 100%, while the conversion of NIPAM was 99%. Furthermore, the molecular weight distribution of this block polymer was measured, and the following values were obtained: $Mn=220,000$ and $Mw=760,000$. The results of measuring the water-gel fraction of this block polymer by a testing method that will be described below are presented in Table 1.

Example 1

The block polymer 1 obtained in Synthesis Example 1 was diluted with methanol, and a 0.5% solution was produced. 60 ul of the solution was added to a 35-mm polystyrene Petri dish (TCPS, manufactured by Iwaki Cell Biology Corp.). Subsequently, the Petri dish was washed by repeating three times an operation of drying the Petri dish for 30 minutes at 80° C. and immersing the Petri dish in pure water for 10 minutes, and the Petri dish was dried overnight at 40° C. Thereby, cell culture substrate 1 was obtained. The results obtained by subjecting this cell culture substrate to an evaluation of cell culturing performance and detachability using a testing methods that will be described below, are presented in Table 1.

(Water-Gel Fraction)

0.1 g of each of the culture substrates was wrapped with a 200-mesh stainless steel wire gauze, and the culture substrate was left to stand in water at 4° C. for 20 hours. Samples obtained before and after the standing were dried for 2 hours in a hot air dryer at 130° C., and the dried weights were respectively measured. Thus, the weight reduction ratio obtained before and after the standing in cold water was investigated. As this value is higher, it can be said that the culture substrate has high water resistance, and elution by water from the culture substrate does not easily occur.

(Evaluation of Cell Culturing Performance)

For the medium, 1 mL of 50 mL fetal bovine serum MEM Non-Essential Amino Acids Solution, 100× (manufactured by Thermo Fisher Scientific, Inc.) and L-Glutamine, 200 mM solution (manufactured by Thermo Fisher Scientific, Inc.) were added to 500 mL of Eagle's minimal essential medium (E-MEM, manufactured by Thermo Fisher Scientific, Inc.). Together with 2 mL of this medium, mouse Balb3T3 cells (JCRB Cell Bank) were inoculated so as to obtain a cell density of $1.0 \times 10^4$ cells/cm$^2$, and culturing performance after three days from inoculation was evaluated by making an observation with a microscope.

◯: The culturing performance is equivalent to the results of culturing with TCPS only without the substrate.

Δ: The culturing performance is poor compared to the results of culturing with TCPS only without the substrate.

x: Cells do not grow at all.

[Evaluation of Cell Detachability]

Balb3T3 cells were cultured on the cell culture substrate 1, and three days after inoculation, a cell detachment test was performed. After the medium in the culture was removed, 1 mL of cold medium at 4° C. was added, and the culture was left to stand for 20 minutes at room temperature of 25° C. The medium was removed from each of detached cells, and then the culture substrate was washed with a phosphate buffered saline (PBS(-)). To the cell culture substrate after being washed, 1 mL of HistoChoice MB Tissue Fixative (manufactured by Amresco, Inc.) was added, remaining cells were fixed thereby for 30 minutes at room temperature, and then the fixative was removed. Subsequently, 1 mL of a 10% Giemsa stain solution was added thereto, and staining was performed for one hour at room temperature. The stain solution was removed, and then the cells were washed with tap water and dried. Cells that had been Giemsa-stained were counted by visual inspection.

◯: The cells were completely detached.

Δ: Some of the cells were detached.

x: The cells were not detached at all.

[Synthesis of Comparative Block Polymer 1]

1.92 g of butyl methacrylate (manufactured by Wako Pure Chemical Industries, Ltd.), 0.06 g of 2-(dodecylthiocarbonothioylthio)propanoic acid as a RAFT agent, 0.012 g of dimethyl 2,2'-azobis(2-methylpropionate), 10.8 g of t-butanol, and 1.2 g of water were subjected to sufficient nitrogen bubbling so as to remove oxygen, and then the mixture was stirred for 7 hours at 70° C. Thus, a first reaction liquid was obtained. The conversion of butyl methacrylate in this stage was 88%.

Next, a mixture of 6.12 g of N-isopropylacrylamide (manufactured by KJ Chemicals Corp.), 18 g of t-butanol, and 2.18 g of water was subjected to sufficient nitrogen bubbling, and then the mixture was added to the above-mentioned reaction liquid. The resultant mixture was further stirred for 20 hours at 70° C., and thereby an AB type temperature-responsive block polymer solution was obtained. The conversions of this block polymer were measured by NMR, and the conversion of butyl methacrylate was 100%, while the conversion of NIPAM was 100%. Furthermore, the molecular weight distribution of this block polymer was measured, and the following values were obtained: $Mn=34,000$ and $Mw=51,000$. The results of measuring the water-gel fraction of this polymer are presented in Table 1.

Comparative Example 1

Comparative block polymer 1 was coated on TCPS according to a method similar to Example 1, and comparative cell culture substrate 1 was produced. The cell culturing performance and detachability thereof were evaluated in the same manner as in Example 1, and results as shown in Table 1 were obtained.

Comparative Example 2

A 35-mm polystyrene Petri dish (TCPS, manufactured by Iwaki Cell Biology Corp.) in a state of not being coated with any cell culture substrate was evaluated in the same manner as in Example 1 for the evaluation of cell culturing performance and detachability, and results as shown in Table 1 were obtained.

TABLE 1

| | | Cell culture substrate | | Evaluation of Balb3T3 cells | |
|---|---|---|---|---|---|
| | Name | Degree of polymerization of lower critical temperature | Water-gel fraction | Culturing performance | Detachability |
| Example 1 | Block polymer 1 | 5000 | 93 | ○ | ○ |
| Comparative Example 1 | Comparative block polymer 1 | 315 | 1 | ○ | Δ |
| Comparative Example 2 | — | — | — | ○ | X |

INDUSTRIAL APPLICABILITY

The cell culture substrate of the present invention is intended to provide a cell culture substrate that enables animal cells to be cultured with high efficiency and enables detachment and harvest of cells after culturing, in a living condition.

The invention claimed is:

1. A cell culture substrate comprising a block polymer comprising a segment having a lower critical solution temperature and a hydrophobic segment,
   wherein the segment having a lower critical solution temperature has a degree of polymerization of 400 to 10,000.

2. The cell culture substrate according to claim 1, wherein the hydrophobic segment is obtainable by polymerizing a monomer represented by the following Formula (1):

[Chem. 1]

$$H_2C = \underset{\underset{R^2}{|}}{\overset{\overset{R^1}{|}}{C}} \quad (1)$$

wherein $R^1$ represents a hydrogen atom or a methyl group; and $R^2$ represents any one of a phenyl group, a carboxyalkyl group having an alkyl with 1 to 8 carbon atoms, a carboxyaralkyl group having an aralkyl with 7 or 8 carbon atoms, a group represented by the following Formula (2), or a group represented by the following Formula (3):

[Chem. 2]

$$-\underset{\underset{O}{\|}}{C}-O-\left[\underset{}{\overset{H_2}{C}}\right]_n-OR^3 \quad (2)$$

wherein n represents 2 or 3; and $R^3$ represents an alkyl group having 1 to 3 carbon atoms,

[Chem. 3]

$$-\underset{\underset{O}{\|}}{C}-\underset{\underset{R^5}{|}}{N}-R^4 \quad (3)$$

wherein $R^4$ and $R^5$ each independently represent a hydrogen atom or an alkyl group having 1 to 6 carbon atoms; and the total number of carbon atoms of $R^4$ and $R^5$ is 5 or more.

3. The cell culture substrate according to claim 1, which is laminated on a supporting medium.

4. The cell culture substrate according to claim 3, which has an average film thickness of 1,000 nm or less.

5. A cell culture equipment comprising a supporting medium and the cell culture substrate according to claim 1.

6. The cell culture substrate according to claim 2, which is laminated on a supporting medium.

7. The cell culture substrate according to claim 6, which has an average film thickness of 1,000 nm or less.

8. A cell culture equipment comprising a supporting medium and the cell culture substrate according to claim 2.

9. A cell culture equipment comprising a supporting medium and the cell culture substrate according to claim 3.

10. A cell culture equipment comprising a supporting medium and the cell culture substrate according to claim 4.

* * * * *